(12) United States Patent
Pitterna et al.

(10) Patent No.: US 6,265,585 B1
(45) Date of Patent: Jul. 24, 2001

(54) PROCESS FOR THE PREPARATION OF THIAZOLE DERIVATIVES

(75) Inventors: Thomas Pitterna, Basel; Peter Maienfisch, Rodersdorf; David John Wadsworth, Bättwil; Laurenz Gsell, Basel; Thomas Rapold; Henry Szczepanski, both of Wallbach, all of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/341,716

(22) PCT Filed: Jan. 20, 1998

(86) PCT No.: PCT/EP98/00297

§ 371 Date: Jul. 15, 1999

§ 102(e) Date: Jul. 15, 1999

(87) PCT Pub. No.: WO98/32747

PCT Pub. Date: Jul. 30, 1998

(30) Foreign Application Priority Data

Jan. 22, 1997 (CH) .................................................. 134/97

(51) Int. Cl.7 ................................................ C07D 277/32
(52) U.S. Cl. ............................................................ 548/203
(58) Field of Search ............................................. 548/203

(56) References Cited

U.S. PATENT DOCUMENTS 4,748,243  5/1988  Beck et al. .

FOREIGN PATENT DOCUMENTS 0 260 560  3/1988  (EP) .
0 446 913  9/1991  (EP) .
WO 96/16050  5/1996  (WO) .

*Primary Examiner*—Robert Gerstl
(74) *Attorney, Agent, or Firm*—William A. Teoli, Jr.

(57) ABSTRACT

A process for the preparation of a compound of formula (I), wherein X is a leaving group; which process comprises, a) for the preparation of a compound of formula (I) wherein X is —OS(=O)$_2$A and A is as defined in the specification, reacting a compound of formula (II) with a sulfonylating agent; or, b) for the preparation of a compound of formula (I) wherein X is iodine, reacting a compound of formula (III) with an iodinating agent, preferably sodium iodide; or, c) for the preparation of a compound of formula (I) whrein X is bromine, reacting a compound of formula (IV) with a brominating agent; or, d) for the preparation of a compound (I) wherein X is chlorine or bromine, reacting a compound (V), wherein R and X are as defined in the specification, with a chlorinating agent, a compound of formula (Ib), the use thereof and a process for the preparation of a compound of formula (II) and a compound of formula (A) are described.

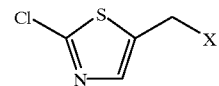

(I)

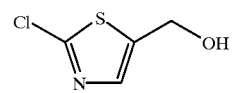

(II)

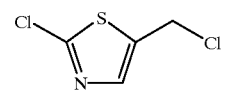

(III)

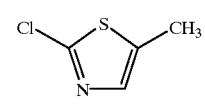

(IV)

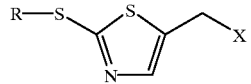

(V)

4 Claims, No Drawings

PROCESS FOR THE PREPARATION OF THIAZOLE DERIVATIVES

The invention relates to a process for the preparation of a compound of formula

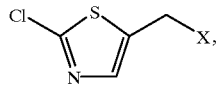
(I)

including, where applicable, an E/Z isomer, a mixture of E/Z isomers, an acid addition product and/or a tautomer thereof, in each case in free form or in salt form, wherein X is a leaving group; which process comprises, a) for the preparation of a compound of formula (I) wherein X is $-OS(=O)_2A$ and A is $C_1-C_8$alkyl, halo-$C_1-C_8$alkyl, hydroxy-$C_1-C_8$alkyl, $C_1-C_8$alkoxy-$C_1-C_8$alkyl, unsubstituted or halo-substituted $C_2-C_8$alkenyl, $C_2-C_4$alkynyl, $C_3-C_7$cycloalkyl or di-($C_1-C_4$alkyl)amine; aryl that is unsubstituted or substituted by halogen, $C_1-C_4$alkyl, $C_1-C_4$alkoxy or by dimethylamine; or unsubstituted or halo-substituted benzyl, reacting a compound of formula

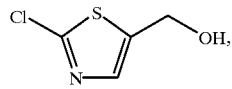
(II)

including, where applicable, an acid addition product and/or a tautomer thereof, in each case in free form or in salt form, with a sulfonylating agent; or, b) for the preparation of a compound of formula (I) wherein X is iodine, reacting a compound of formula

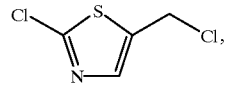
(III)

including, where applicable, an acid addition product and/or a tautomer thereof, in each case in free form or in salt form, with an iodinating agent, preferably sodium iodide; or, c) for the preparation of a compound of formula (I) wherein X is bromine, reacting a compound of formula

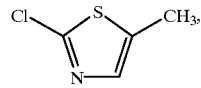
(IV)

including, where applicable, an acid addition product and/or a tautomer thereof, in each case in free form or in salt form, with a brominating agent, preferably in the presence of a radical initiator, or, d) for the preparation of a compound of formula (I) wherein X is chlorine or bromine, reacting with a chlorinating agent a compound of formula

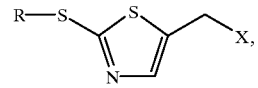
(V)

including, where applicable, an E/Z isomer, a mixture of E/Z isomers, an acid addition product and/or a tautomer thereof, in each case in free form or in salt form, wherein X is as defined for formula (I) above, and R is unsubstituted or substituted $C_1-C_{12}$alkyl, unsubstituted or substituted $C_2-C_4$alkenyl, unsubstituted or substituted $C_2-C_4$alkynyl, unsubstituted or substituted $C_3-C_6$cycloalkyl, unsubstituted or substituted aryl, unsubstituted or substituted heteroaryl, or $-SR_6$, and $R_6$ is unsubstituted or substituted $C_1-C_{12}$alkyl, unsubstituted or substituted $C_2-C_4$alkenyl, unsubstituted or substituted $C_2-C_4$alkynyl, unsubstituted or substituted $C_1-C_6$cycloalkyl, unsubstituted or substituted aryl, or unsubstituted or substituted heteroaryl;

and, in each case, if desired, converting a compound of formula (I) obtainable in accordance with the process or by another method, or an E/Z isomer, acid addition product or tautomer thereof, in each case in free form or in salt form, into a different compound of formula (I) or an E/Z isomer, acid addition product or tautomer thereof, in each case in free form or in salt form, separating a mixture of E/Z isomers obtainable in accordance with the process and isolating the desired isomer, and/or converting a free compound of formula (I) obtainable in accordance with the process or by another method, or an E/Z isomer or tautomer thereof, into a salt or converting a salt, obtainable in accordance with the process or by another method, of a compound of formula (I) or of an E/Z isomer or tautomer thereof into the free compound of formula (I) or an E/Z isomer or tautomer thereof or into a different salt.

Methods of synthesis for the compounds of formula (I) are described in the literature but they are not entirely satisfactory. There is therefore a need to make available improved processes for the preparation of those compounds.

The compounds of formula (I) are valuable intermediates which can be used in the preparation of pesticidally active compounds, especially the compounds, known per se, of formula

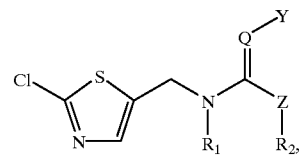
(A)

and, where applicable, the E/Z isomers, mixtures of E/Z isomers, acid addition products and/or tautomers thereof, in each case in free form or in salt form, wherein Q is CH or N, Y is $NO_2$ or CN, Z is $CHR_3$, O, $NR_3$ or S, $R_1$ and $R_2$ either are, each independently of the other, hydrogen or alkyl that is unsubstituted or substituted by $R_4$ or together form a two- or three-membered alkylene bridge which may contain a hetero atom from the group consisting of $NR_5$, O and S, $R_3$ is H or alkyl that is unsubstituted or substituted by $R_4$, $R_4$ is unsubstituted or substituted aryl or heteroaryl, and $R_5$ is H or alkyl.

The invention therefore relates also to a process known per se for the preparation of compounds of formula (A) from a compound of formula (I) prepared in accordance with the process of the invention.

Some compounds of formula (I) contain asymmetric carbon atoms, as a result of which the compounds may occur in optically active forms. Formula (I) is intended to include all those possible isomeric forms, and mixtures thereof, for example race-mates or mixtures of E/Z isomers.

The general terms used hereinbefore and hereinafter have the following meanings, unless defined otherwise:

Carbon-containing groups and compounds each contain from 1 up to and including 8, preferably from 1 up to and including 6, especially from 1 up to and including 4, and more especially 1 or 2, carbon atoms.

Alkyl, both as a group per se and as a structural element of other groups and compounds, for example haloalkyl, alkoxyalkyl and hydroxyalkyl, is, in each case taking due account of the number of carbon atoms contained in the group or compound in question, either straight-chained, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl, both as a group per se and as a structural element of other groups and compounds, for example haloalkenyl and arylalkenyl, is, in each case taking due account of the number of carbon atoms contained in the group or compound in question, either straight-chained, for example vinyl, 1-methylvinyl, allyl, 1-butenyl or 2-hexenyl, or branched, for example isopropenyl.

Alkynyl, both as a group per se and as a structural element of other groups and compounds, for example haloalkynyl, is, in each case taking due account of the number of carbon atoms contained in the group or compound in question, either straight-chained, for example propargyl, 2-butynyl or 5-hexynyl, or branched, for example 2-ethynylpropyl or 2-propargylisopropyl.

$C_3$–$C_6$Cycloalkyl is cyclopropyl, cyclobutyl, cyclopentyl or cyclohexyl, especially cyclohexyl.

Aryl is phenyl or naphthyl, especially phenyl.

Heteroaryl is to be understood as being a five- to seven-membered monocyclic aromatic ring having from one to three hetero atoms selected from the group consisting of N, O and S, especially N and S, or a bicyclic heteroaryl that may contain, either in only one ring (as, for example, in quinolinyl, quinoxalinyl, indolinyl, benzothiophenyl or benzofuranyl) or in both rings (as, for example, in pteridinyl or purinyl), one or more hetero atoms, independently of one another, selected from N, O and S. Preference is given to pyridyl, pyrimidinyl, thiazolyl and benzothiazolyl, especially thiazolyl.

Halogen, both as a group per se and as a structural element of other groups and compounds, for example haloalkyl, haloalkenyl and haloalkynyl, is fluorine, chlorine, bromine or iodine, especially fluorine, chlorine or bromine, more especially chlorine or bromine, and very especially chlorine.

Halo-substituted, carbon-containing groups and compounds, for example haloalkyl, haloalkenyl and haloalkynyl, may be partially halogenated or perhalogenated, the halogen substituents in the case of multiple halogenation being identical or different. Examples of haloalkyl, both as a group per se and as a structural element of other groups and compounds, for example haloalkenyl, are methyl mono- to tri-substituted by fluorine, chlorine and/or by bromine, for example $CHF_2$ or $CF_3$; ethyl mono- to penta-substituted by fluorine, chlorine and/or by bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each mono- to hepta-substituted by fluorine, chlorine and/or by bromine, for example $CH_2CHBrCH_2Br$, $CF_2CHFCF_3$, $CH_2CF_2CF_3$ or $CH(CF_3)_2$; and butyl, or one of the isomers thereof, mono- to nona-substituted by fluorine, chlorine and/or by bromine, for example $CF(CF_3)CHFCF_3$ or $CH_2(CF_2)_2CF_3$. Haloalkenyl is, for example, $CH_2CH=CHCl$, $CH_2CH=CCl_2$, $CH_2CF=CF_2$ or $CH_2CH=CHCH_2Br$.

Some compounds of formula (I) may be in the form of tautomers. The compounds of formula (I) are therefore to be understood hereinbefore and hereinafter as including corresponding tautomers, even if the latter are not specifically mentioned in each case.

According to the invention, acid addition products are to be understood as being products obtainable by addition of an acid, preferably an inorganic acid, to a double bond, especially to a double bond in a heterocycle. For example, the addition of $HX_1$, wherein the anion $X_1$ is as defined for X in formula (I) above, to a compound of formula (I), as defined hereinbefore, yields a compound of formula

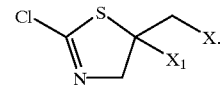

(Ia)

The person skilled in the art will be aware that an acid $HX_1$ can also be readily removed from the said acid addition product; for example, the compound of formula (Ia) can be readily converted back into a compound of formula (I). The compounds of formulae (I) to (V) and (A) are therefore to be understood hereinbefore and hereinafter as including both the free compounds of formulae (I) to (V) and (A) and the corresponding acid addition products, in free form or in salt form, even if that is not explicitly mentioned in each individual case.

Compounds of formula (I) having at least one basic centre are capable, for example, of forming acid addition salts. Those acid addition salts are formed, for example, with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted or substituted, e.g. halo-substituted, $C_1$–$C_4$alkane-carboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$–$C_4$alkane- or aryl-sulfonic acids, e.g. methane- or p-toluene-sulfonic acid. Furthermore, compounds of formula (I) having at least one acid group are capable of forming salts with bases. Suitable salts with bases are, for example, metal salts, such as alkali metal and alkaline earth metal salts, e.g. sodium, potassium and magnesium salts, and salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally also be formed. The compounds of formula (I) are to be understood hereinbefore and hereinafter as including both the compounds of formula (I) in free form and the corresponding salts. The same is correspondingly true for the acid addition products and tautomers of compounds of formula (I) and salts thereof. In each case preference is generally given to a process for the preparation of the free form.

A leaving group X is to be understood hereinbefore and hereinafter as being any removable group customarily considered for chemical reactions, as will be known to the person skilled in the art, especially chlorine, bromine, iodine, —OS(=O)$_2$A or —S(=O)$_2$A wherein A is unsubstituted or substituted $C_1$–$C_8$alkyl, $C_2$–$C_8$alkenyl or $C_2$–$C_8$alkynyl, unsubstituted or substituted aryl, unsubstituted or substituted benzyl or di($C_1$–$C_8$alkyl)-amine wherein the alkyl groups are independent of one another; $NO_3$, $NO_2$, or sulfate, sulfite, phosphate, phosphite, carboxylate, imino ester, $N_2$ or carbamate. Especially preferred leaving groups are chlorine, bromine, iodine, methanesulfonate, trifluoromethanesulfonate, ethanesulfonate, 2,2,2-trifluoroethanesulfonate, perfluoronbutanesulfonate, benzenesulfonate or benzenesulfonate substituted by methyl, chlorine, bromine or by nitro. Very especially preferred leaving groups are mentioned in the individual processes.

Preference is given within the scope of the invention to a process for the preparation of a compound of formula (I)
(1) wherein X is —OS(=O)$_2$A and A is $C_1$–$C_8$alkyl, halo-$C_1$–$C_8$alkyl, hydroxy-$C_1$–$C_8$alkyl, $C_1$–$C_4$alkoxy-$C_1$–$C_8$alkyl, unsubstituted or halo-substituted $C_2$–$C_4$alkenyl, $C_2$–$C_4$alkynyl, $C_3$–$C_6$cycloalkyl or di($C_1$–$C_4$alkyl)amine, aryl that is unsubstituted or substituted by halogen, $C_1$–$C_4$alkyl or by dimethylamine, or unsubstituted or chloro-substituted benzyl;
especially wherein A is $C_1$–$C_4$alkyl, halo-$C_1$–$C_4$alkyl, $C_3$–$C_4$alkenyl, $C_3$–$C_4$alkynyl, phenyl that is unsubstituted or substituted by chlorine or by methyl, unsubstituted or chloro-substituted benzyl, or cyclohexyl; more especially $C_1$–$C_4$alkyl, $CF_3$, $CH_2CF_3$, phenyl, 4-chlorophenyl, p-tolyl, benzyl, cyclohexyl; very especially methyl, ethyl, phenyl or benzyl;
(2) wherein X is bromine;
(3) wherein X is iodine;
(4) wherein X is chlorine;
(5) wherein R in the compounds of formula (V) is $C_1$–$C_{12}$alkyl that is unsubstituted or substituted by halogen, OH or by SH; unsubstituted or halo-substituted aryl-$C_1$–$C_4$alkyl, unsubstituted or halo-substituted heteroaryl-$C_1$–$C_4$alkyl, aryl-$C_1$–$C_4$alkenyl or heteroaryl-$C_1$–$C_4$alkenyl; unsubstituted or halo-substituted $C_2$–$C_4$alkenyl, $C_2$–$C_4$alkynyl, aryl-$C_2$–$C_4$alkynyl, heteroaryl-$C_2$–$C_4$alkynyl or $C_4$–$C_6$cycloalkyl; aryl that is unsubstituted or substituted by halogen, $C_1$–$C_4$alkyl, HO—$C_1$–$C_4$alkyl or by HS—$C_1$–$C_4$alkyl; heteroaryl that is unsubstituted or substituted by halogen or by $C_1$–$C_4$alkyl; —$CH_2$—COO—$C_1$–$C_8$alkyl, —$CH_2$—CO—$C_1$–$C_8$alkyl, $SR_6$, —$(CH_2)_n$—$SR_6$ or —$CH_2$—COO—M wherein M is hydrogen or a cation equivalent and n is from 1 to 8;
especially $C_1$–$C_{12}$alkyl that is unsubstituted or substituted by halogen, OH or by SH; unsubstituted or halo-substituted aryl-$C_1$–$C_4$alkyl, unsubstituted or halo-substituted heteroaryl-$C_1$–$C_4$alkyl, aryl-$C_1$–$C_4$alkenyl or heteroaryl-$C_1$–$C_4$alkenyl; unsubstituted or halo-substituted $C_2$–$C_4$alkenyl, $C_2$–$C_4$alkynyl, aryl-$C_2$–$C_4$alkynyl, heteroaryl-$C_2$–$C_4$alkynyl or $C_4$–$C_6$cycloalkyl; aryl that is unsubstituted or substituted by halogen, $C_1$–$C_4$alkyl, HO—$C_1$–$C_4$alkyl or by HS—$C_1$–$C_4$alkyl; heteroaryl that is unsubstituted or substituted by halogen or by $C_1$–$C_4$alkyl; —$CH_2$—COO—$C_1$–$C_8$alkyl, —$CH_2$—CO—$C_1$–$C_8$alkyl, $SR_6$, —$(CH_2)_n$—$SR_6$ or —$CH_2$—COO—M wherein M is hydrogen, an alkali metal or (alkyl)$_4$N and n is from 1 to 8;
more especially $C_1$–$C_4$alkyl, hydroxy-$C_1$–$C_4$alkyl, $C_3$–$C_4$alkenyl, $C_3$–$C_4$alkynyl, chloro-$C_3$–$C_4$alkenyl, phenyl that is unsubstituted or substituted by chlorine, benzyl that is unsubstituted or substituted by chlorine, heteroaryl, cyclohexyl, —$CH_2$—COO—$C_1$–$C_4$alkyl; very especially $C_1$–$C_4$alkyl, phenyl, benzyl, cyclohexyl, benzothiazol-2-yl, —$CH_2$—COO— ethyl or —$CH_2$—COO—Na;
most especially phenyl or benzyl.

The present invention relates also to a process for the preparation of a compound of formula (II), including, where applicable, an acid addition product and/or a tautomer thereof, in each case in free form or in salt form, which process comprises
e) reacting a compound of formula (III) with a base;
and, in each case, if desired, converting a compound of formula (II) obtainable in accordance with the process or by another method, or an acid addition product or tautomer thereof, in each case in free form or in salt form, into a different compound of formula (II) or an acid addition product or tautomer thereof, in each case in free form or in salt form, or converting a free compound of formula (II) obtainable in accordance with the process or by another method, or an acid addition product or tautomer thereof, into a salt or converting a salt, obtainable in accordance with the process or by another method, of a compound of formula (II) or of an acid addition product or tautomer thereof into the free compound of formula (II) or an acid addition product or tautomer thereof or into a different salt.

The invention relates also to a compound of formula

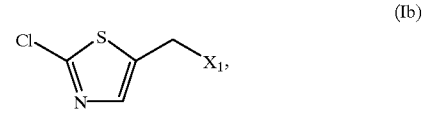

(Ib)

including, where applicable, an E/Z isomer, a mixture of E/Z isomers, an acid addition product and/or a tautomer thereof, in each case in free form or in salt form,
wherein $X_1$ is iodine, —OS(=O)$_2$A or S(=O)$_2$A, and
A is unsubstituted or substituted $C_1$–$C_8$alkyl, $C_2$–$C_8$alkenyl or $C_2$–$C_8$alkynyl, unsubstituted or substituted aryl, unsubstituted or substituted benzyl or di($C_1$–$C_8$alkyl)amine wherein the alkyl groups are independent of one another;
especially wherein $X_1$ is iodine or —OS(=O)$_2$A and A is $C_1$–$C_8$alkyl, halo-$C_1$–$C_8$alkyl, hydroxy-$C_1$–$C_3$alkyl, $C_1$–$C_8$alkoxy-$C_1$–$C_8$alkyl, unsubstituted or halo-substituted $C_2$–$C_8$alkenyl, $C_2$–$C_4$alkynyl, $C_3$–$C_7$cycloalkyl or di($C_1$–$C_4$alkyl)amine, aryl that is unsubstituted or substituted by halogen, $C_1$–$C_4$alkyl, $C_1$–$C_4$alkoxy or by dimethylamine, or unsubstituted or halo-substituted benzyl;
more especially wherein $X_1$ is iodine.

The remarks made above in relation to the acid addition products, E/Z isomers and tautomers, in free form or in salt form, of the compounds of formulae (I) and (Ia) apply analogously to the starting materials of formulae (II) to (V) referred to hereinbefore and hereinafter, in respect of the acid addition products, E/Z isomers and tautomers thereof, in free form or in salt form.

The reactions of variants a) to e) described hereinbefore and hereinafter are carried out in a manner known per se, for example in the absence or, usually, in the presence of a suitable solvent or diluent or of a mixture thereof, the reactions being carried out as required with cooling, at room temperature or with heating, for example in a temperature range from approximately −80° C. to the boiling temperature of the reaction medium, preferably from approximately −20° C. to approximately +120° C., especially from 20° C. to 80° C., and, if necessary, in a closed vessel, under pressure, in an inert gas atmosphere and/or under anhydrous conditions. Especially advantageous reaction conditions can be found in the Examples.

The reactants can be reacted with one another as such, i.e. without the addition of a solvent or diluent, for example in the melt. In most cases, however, the addition of an inert solvent or diluent, or of a mixture thereof, is advantageous. Examples of such solvents or diluents that may be mentioned are: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; ketones, such as acetone, methyl ethyl ketone and methyl isobutyl ketone; alcohols, such as methanol, ethanol, propanol, isopropanol, butanol, ethylene glycol and glycerol; amides, such as N,N-dimethylformamide, N,N-diethylformamide, N,N-dimethylacetamide, N-methylpyrrolidone and hexamethylphosphoric acid triamide; nitriles, such as acetonitrile and propionitrile; and sulfoxides, such as dimethyl sulfoxide. If the reaction in question is carried out in the presence of a base, bases used in excess, such as triethylamine, pyridine, N-methylmorpholine and N,N-diethylaniline, may also serve as solvents or diluents. If the reaction is carried out in the presence of an acid catalyst, acids used in excess, for example strong organic carboxylic acids, such as unsubstituted or substituted, for example halo-substituted, $C_1$–$C_4$alkanecarboxylic acids, e.g. formic acid, acetic acid and propionic acid, may also serve as solvents or diluents. Suitable solvents for each reaction can be found in the Examples given below.

When bases are added to the reaction mixture, those bases are, for example, alkali metal or alkaline earth metal hydroxides, hydrides, amides, alkanolates, acetates, carbonates, dialkylamides and alkylsilylamides; alkylamines, alkylenediamines, free or N-alkylated, saturated or unsaturated cycloalkylamines, basic heterocycles, ammonium hydroxides and carbocyclic amines. Examples are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyl-trimethyl-ammonium hydroxide and 1,5-diazabicyclo[5.4.0]undec-5-ene (DBU). Preferred bases are mentioned in the individual reaction steps.

Variant a):

The reaction is preferably carried out in a temperature range from −20 to 160° C., especially from 0 to 100° C., preferably from 0 to 25° C.

Solvents that are inert under the prevailing reaction conditions are used, such as aliphatic and aromatic hydrocarbons, for example petroleum ether, pentane, hexane, heptane, toluene or a xylene; halogenated hydrocarbons, for example chlorobenzene, methylene chloride, ethylene chloride, bromochloromethane, chloroform, carbon tetrachloride and tetrachloroethylene; lower carboxylic acids, for example formic acid and acetic acid; esters, preferably ethyl acetate; nitriles, for example acetonitrile; amides, for example dimethylformamide and dimethylacetamide; ethers, for example diethyl ether, diisopropyl ether, tetrahydrofuran and dioxane; or a mixture thereof. Preference is given to tetrahydrofuran, methylene chloride, toluene, dioxane, chlorobenzene, bromochloromethane, ethyl acetate and acetonitrile; special preference is given to tetrahydrofuran, methylene chloride, toluene, acetonitrile, ethyl acetate and dioxane.

Suitable sulfonylating agents are: sulfonic anhydrides and sulfonic acid chlorides, for example methanesulfonic anhydride, methanesulfonic acid chloride, trifluoromethanesulfonic acid chloride and 4-toluenesulfonic acid chloride.

It is usual to add to the reaction mixture a base of the kind mentioned at the beginning, preferably an alkali metal or alkaline earth metal carbonate, hydrogen carbonate or hydroxide, or a tertiary amine; especially potassium carbonate, triethylamine, pyridine, 4-(N,N-dimethylamino)-pyridine, ethyl diisopropylamine, and mixtures thereof.

Variant b):

The reaction is preferably carried out in a temperature range from −20 to 160° C., especially from 0 to 100° C., preferably from 0 to 80° C.

Solvents that are inert under the prevailing reaction conditions are used, such as aliphatic and aromatic hydrocarbons, halogenated hydrocarbons, esters, ketones, nitriles, amides, ethers, and a mixture of water and a halogenated hydrocarbon; preference is given to acetone, methyl ethyl ketone, petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, toluene, dimethylformamide, dimethylacetamide, diethyl ether, diisopropyl ether, tetrahydrofuran and dioxane, or mixtures thereof, especially two-phase systems; special preference is given to acetone and to a mixture of water and methylene chloride.

Suitable iodinating agents are: iodides, for example alkali metal iodides and tetraalkylammonium iodides; sodium iodide is preferred.

To the reaction mixture there is optionally added a phase transfer catalyst, preferably a tetraalkylammonium salt; especially tetrabutylammonium iodide or tetrabutylammonium chloride; in another preferred form of the process, no phase transfer catalyst is added to the reaction mixture.

Variant c):

The reaction is preferably carried out in a temperature range from −20 to 160° C., especially from 0 to 100° C., preferably from 0 to 80° C.

Solvents as mentioned under variant a) and that are inert under the prevailing reaction conditions are used; especially halogenated hydrocarbons, for example methylene chloride, ethylene chloride, bromochloromethane, chloroform and carbon tetrachloride; or a mixture thereof; carbon tetrachloride is preferred.

Suitable brominating agents are bromine and N-bromine imides, especially bromine, N-bromosuccinimide and dibromohydantoin.

A radical initiator is added to the reaction mixture; examples that may be mentioned are irradiation with UV light, diacyl peroxides and azo compounds; preference is given to dibenzoyl peroxide, azoisobutyronitrile and UV light.

Variant d):

Suitable chlorinating agents are, for example, elemental chlorine, sulfonyl chloride, Javelle water, polysulfur dichloride, sulfur dichloride, phosphorus trichloride, phosphorus pentachloride or mixtures of two or more of those reagents; especially elemental chlorine, sulfonyl chloride, Javelle water, sulfur dichloride or a mixture of those compounds, more especially chlorine.

The reactants can be reacted with one another as such, i.e. without a solvent or diluent, for example in the melt. In most cases, however, the addition of a solvent or diluent is advantageous. Examples of such solvents or diluents are: water; acids, for example hydrochloric acid, sulfuric acid, formic acid and acetic acid; aromatic, aliphatic and alicyclic hydrocarbons and halogenated hydrocarbons, for example benzene, toluene, xylene, mesitylene, Tetralin, chlorobenzene, dichlorobenzene, bromobenzene, petroleum ether, hexane, cyclohexane, dichloromethane, trichloromethane, carbon tetrachloride, dichloroethane, trichloroethene and tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; ketones, such as acetone, methyl ethyl ketone and methyl isobutyl ketone; alcohols, such as methanol, ethanol, propanol, isopropanol, butanol, ethylene glycol and glycerol; amides, such as N,N-dimethylformamide, N,N-diethylformamide, N,N-dimethylacetamide, N-methylpyrrolidone and hexamethylphosphoric acid triamide; nitriles, such as acetonitrile and propionitrile; and sulfoxides, such as dimethyl sulfoxide; or mixtures of such solvents. In a preferred form of the process, the reaction is carried out in a halogenated hydrocarbon, especially dichloromethane.

The reaction is preferably carried out at a temperature from 0° C. to +180° C., especially from +10° C. to +80° C., in many cases from room temperature to the reflux temperature of the solvent. In a preferred form of variant d), the reaction is carried out at from 0° C. to 120° C., especially from 10° C. to 40° C.

The reaction is preferably carried out under normal pressure.

The reaction time is not critical; preference is given to a reaction time of from 0.1 to 48 hours, especially from 2 to 12 hours.

The product is isolated by the usual methods, for example by filtration, crystallisation, distillation or chromatography, or any suitable combination of such methods.

Variant e):

The reaction is preferably carried out in a temperature range from −20 to 160° C., especially from 0 to 100° C., preferably from 0 to 80° C.

Solvents as mentioned under variant a) and that are inert under the prevailing reaction conditions are used; suitable solvents are especially nitriles, amides, ethers, ketones and water; more especially acetone, methyl ethyl ketone, acetonitrile, dimethylformamide, dimethylacetamide, tetrahydrofuran, dioxane and water; or mixtures thereof; special preference is given to a mixture of dioxane and water.

It is usual to add a base of the kind mentioned at the beginning; preferably an alkali metal carbonate, alkali metal hydrogen carbonate or alkali metal hydroxide; sodium hydrogen carbonate is especially preferred.

Depending on the procedure and reaction conditions, the compounds of formulae (I) and (II) having salt-forming properties may be obtained in free form or in the form of salts.

The compounds of formula (I), in each case in free form or in salt form, may be in the form of one of the possible isomers or in the form of a mixture thereof, for example depending on the number of asymmetric carbon atoms in the molecule and the absolute and relative configuration thereof and/or depending on the configuration of non-aromatic double bonds in the molecule they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood hereinbefore and hereinafter, even if stereochemical details are not specifically mentioned in each case.

Mixtures of diastereoisomers and mixtures of racemates of compounds of formula (I), or salts thereof, obtainable in accordance with the process depending on the starting materials and procedures chosen or by other means, can be separated on the basis of the physicochemical differences between the constituents into the pure diastereoisomers or racemates in known manner, for example by fractional crystallisation, distillation and/or chromatography.

Mixtures of enantiomers, such as racemates, so obtainable can be resolved into the optical antipodes by known methods, for example by recrystallisation from an optically active solvent, by chromatography on chiral adsorbents, e.g. high-pressure liquid chromatography (HPLC) on acetyl cellulose, with the aid of suitable microorganisms, by cleavage with specific immobilised enzymes, via the formation of inclusion compounds, e.g. using chiral crown ethers, in which case only one enantiomer is complexed, or by conversion into diastereoisomeric salts, e.g. by reaction of a basic end product racemate with an optically active acid, such as a carboxylic acid, e.g. camphoric, tartaric or malic acid, or a sulfonic acid, e.g. camphorsulfonic acid, and separation of the resulting mixture of diastereoisomers, e.g. on the basis of their different solubilities by fractional crystallisation, into the diastereoisomers from which the desired enantiomer can be freed by the action of suitable, e.g. basic, agents.

Apart from by separation of corresponding mixtures of isomers, it is possible according to the invention to obtain pure diastereoisomers or enantiomers also by generally known methods of diastereoselective or enantioselective synthesis, for example by carrying out the process according to the invention using starting materials having a correspondingly suitable stereochemistry.

The compounds of formulae (I) and (II), acid addition products and the salts thereof can also be obtained in the form of their hydrates and/or can include other solvents, for example solvents which may have been used for the crystallisation of compounds occurring in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes or, especially, is formed under the reaction conditions.

Compounds of formula (I) obtainable in accordance with the process or by other means may be converted into different compounds of formula (I) in a manner known per se.

In the process of the present invention there are preferably used those starting materials and intermediates, in each case in free form or in salt form, which result in the compounds of formulae (I) and (II), or salts thereof, described at the beginning as being especially valuable.

The invention relates especially to the preparation processes described in Examples P1 and P2.

The compounds of formulae (II), (III), (IV) and (V) are known.

PREPARATION EXAMPLES

Example P1
2-Chloro-5-hydroxymethyl-thiazole

A mixture of 30 g of 2-chloro-5-chloromethyl-thiazole, 15.8 g of sodium hydrogen carbonate, 200 ml of dioxane and 200 ml of water is stirred for 24 hours at room temperature. After addition of 500 ml of diethyl ether, the organic phase is separated off and concentrated to dryness by evaporation. The residue is chromatographed on silica gel using ethyl acetate/hexane (1:1), yielding the title compound having a refractive index $n_D^{23}$ of 1.5702.

Example P2a)
Preparation of 5-bromomethyl-2-chloro-thiazole:

1.0 g of 2-chloro-5-methyl-thiazole, 36 mg of dibenzoyl peroxide and 1.6 g of N-bromosuccinimide are heated in carbon tetrachloride for 36 hours under reflux. The mixture is then cooled to room temperature and filtered. The solvent is evaporated off and the residue is purified by chromatography on silica gel using hexane/ethyl acetate, yielding 5-bromomethyl-2-chloro-thiazole having a melting point of 32° C. (compound 1.1).

Example P2b)
Preparation of 5-iodomethyl-2-chloro-thiazole:

4.46 g of sodium iodide are added to 5.0 g of 2-chloro-5-chloromethyl-thiazole in 40 ml of acetone. The reaction mixture is stirred for 2 hours at room temperature; 100 ml of diethyl ether are added and the mixture is filtered. The solvent is evaporated off, yielding the title compound having a melting point of 20–25° C. (compound 1.2).

Example P2c)
Preparation of 2-chloro-5-methylsulfonyloxymethyl-thiazole:

1.28 g of methanesulfonic anhydride are added to 1.0 g of 2-chloro-5-hydroxymethyl-thiazole and 0.63 g of pyridine in 10 ml of tetrahydrofuran and the mixture is stirred for three hours at room temperature. Concentration of the solution yields the title compound in the form of a solid (compound 1.3). $^1$H-NMR (DMSO-$d_6$, 250 MHz): s, 1H, 7.87 ppm; s, 2H, 5.52 ppm; s, 3H, 2.43 ppm.

Example P2d)
Preparation of 2-chloro-5-chloromethyl-thiazole:

2 g of 2-benzylthio-5-chloromethyl-thiazole are dissolved in 20 ml of dichloromethane. Chlorine is introduced for 30 minutes at 20° C. The reaction mixture is heated under reflux for 2 hours and then concentrated using a rotary evaporator. The residue is purified by chromatography on silica gel (eluant: dichloromethane), yielding the title compound having a melting point of 34° C. (compound 1.4).

Example P2e)

The other compounds listed in Table 1 can also be prepared in a manner analogous to that described in Examples P1 and P2.

TABLE 1

Compounds of the formula

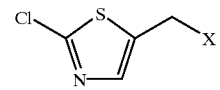

| Comp. No. | X | Phys. data |
|---|---|---|
| 1.1 | Br | m.p. 32° C. |
| 1.2 | I | m.p. 25–30° C. |
| 1.3 | —O—S(=O)$_2$—CH$_3$ | |
| 1.4 | Cl | m.p. 34° C. |
| 1.5 | —O—S(=O)$_2$—CH$_2$—CH$_3$ | |
| 1.6 | —O—S(=O)$_2$—CF$_3$ | |
| 1.7 | —O—S(=O)$_2$—C$_4$F$_9$ | |
| 1.8 | —O—S(=O)$_2$—CH$_2$—CF$_3$ | |
| 1.9 | —O—S(=O)$_2$—C$_6$H$_5$ | |
| 1.10 | —O—S(=O)$_2$—C$_6$H$_4$—CH$_3$ | |
| 1.11 | —O—S(=O)$_2$—C$_6$H$_4$—Br | |
| 1.12 | —O—S(=O)$_2$—C$_6$H$_4$—NO$_2$ | |

TABLE 1-continued

Compounds of the formula

| Comp. No. | X | Phys. data |
|---|---|---|
| 1.13 | 2,4,6-trimethylphenyl-SO₂-O- | |
| 1.14 | 2,5-dichlorophenyl-SO₂-O- | |
| 1.15 | 5-(dimethylamino)naphthyl-SO₂-O- | |
| 1.16 | (CH₃)₂N-SO₂-O- | |

Example P3
Preparation of 5-(2-chlorothiazol-5-ylmethyl)-3-methyl-4-nitroimino-perhydro-1,3,5-oxadiazine (Compound 2-2)

a) 10 ml of dimethylformamide, 2.31 g of potassium carbonate and 1.07 g of 3-methyl-4-nitroimino-perhydro-1,3,5-oxadiazine are added to a solution of 2-chloro-5-methyl-sulfonyloxymethyl-thiazole in tetrahydrofuran. The mixture is stirred for 16 hours at 50° C., cooled to room temperature and filtered; the filtrate is concentrated to dryness by evaporation. The residue is purified by column chromatography on silica gel using dichloromethane/methanol (9:1), yielding the title compound having a melting point of 131–133° C.

b) A mixture of 2.0 g of 2-chloro-5-iodomethyl-thiazole, 20 ml of dimethylformamide, 2.66 g of potassium carbonate and 1.23 g of 3-methyl-4-nitroimino-perhydro-1,3,5-oxadiazine is stirred for 16 hours at 50° C., cooled to room temperature and filtered; the filtrate is concentrated to dryness by evaporation. The residue is purified by column chromatography on silica gel using dichloromethane/methanol (9:1), yielding the title compound having a melting point of 132-134° C.

c) 3.18 g of 5-bromomethyl-2-chloro-thiazole, 12 ml of dimethylformamide, 1.99 g of 3-methyl-4-nitroimino-perhydro-1,3,5-oxadiazine and 3.79 g of potassium carbonate are combined and the mixture is stirred for 5 hours at 50° C. The mixture is cooled to room temperature and 50 ml of water and 50 ml of dichloromethane are added. The organic phase is separated off and dried over magnesium sulfate; the solvent is evaporated off in vacuo. The residue is purified by column chromatography on silica gel using hexane/ethyl acetate (1:1), yielding the title compound (compound 2-2).

d) 2.5 g of 2-chloro-5-chloromethyl-thiazole, 12 ml of dimethylformamide, 2 g of 3-methyl-4-nitroimino-perhydro-1,3,5-oxadiazine and 3.8 g of potassium carbonate are combined and the mixture is stirred for 5 hours at 50° C. The mixture is cooled to room temperature and 50 ml of water and 50 ml of dichloromethane are added. The organic phase is separated off and dried over magnesium sulfate; the solvent is evaporated off in vacuo. Purification is carried out by column chromatography on silica gel using hexane/ethyl acetate (1:1), yielding the title compound (compound 2-2).

Example P3e

The other compounds listed in Table 2 can also be prepared in a manner analogous to that described in Examples P3a) to P3d).

TABLE 2

Compounds of the formula

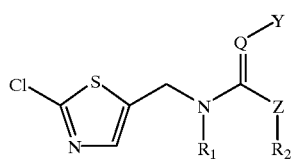

| No. | R₁ | R₂ | Z | Q-Y | M.p.(° C.) |
|---|---|---|---|---|---|
| 2-1 | —CH₂—O—CH₂— | | NH | N—NO₂ | 146° C. |
| 2-2 | —CH₂—O—CH₂— | | N—CH₃ | N—NO₂ | 132–134° C. |
| 2-3 | —CH₂—O—CH₂— | | N—CH₂—CH₃ | N—NO₂ | |
| 2-4 | —CH₂—O—CH₂— | | N—CH₂—CH₂—CH₃ | N—NO₂ | |
| 2-5 | —CH₂—O—CH₂— | | N-n-C₄H₉ | N—NO₂ | 73° C. |
| 2-6 | —CH₂—O—CH₂— | | N—CH₂—CH=CH₂ | N—NO₂ | |
| 2-7 | —CH₂—O—CH₂— | | N—CH₂—C≡CH | N—NO₂ | 176° C. |
| 2-8 | —CH₂—N(CH₃)—CH₂— | | NH | N—NO₂ | |
| 2-9 | —CH₂—N(CH₃)—CH₂— | | N—CH₃ | N—NO₂ | |
| 2-10 | —CH₂—N(CH₂—CH₃)—CH₂— | | NH | N—NO₂ | |

TABLE 2-continued

Compounds of the formula

| No. | R₁ | R₂ | Z | Q-Y | M.p.(° C.) |
|---|---|---|---|---|---|
| 2-11 | —CH₂—N(CH₂—CH₃)—CH₂— | | N—CH₃ | N—NO₂ | |
| 2-12 | —CH₂—N(n-C₃H₇)—CH₂— | | NH | N—NO₂ | |
| 2-13 | —CH₂—N(n-C₃H₇)—CH₂— | | N—CH₃ | N—NO₂ | |
| 2-14 | —CH₂—N(CH₂—CH(CH₃)₂)—CH₂— | | NH | N—NO₂ | |
| 2-15 | —CH₂—N(CH₂—CH(CH₃)₂)—CH₂— | | N—CH₃ | N—NO₂ | |
| 2-16 | —CH₂—CH₂—CH₂— | | NH | N—NO₂ | 125° C. |
| 2-17 | —CH₂—CH₂—CH₂— | | N—CH₃ | N—NO₂ | |
| 2-18 | —CH₂—CH₂— | | NH | N—NO₂ | 150° C. |
| 2-19 | —CH₂—CH₂— | | N—CH₃ | N—NO₂ | 112° C. |
| 2-20 | H | CH₃ | NH | N—NO₂ | |
| 2-21 | CH₃ | H | NH | N—NO₂ | |
| 2-22 | H | H | NH | N—NO₂ | |
| 2-23 | CH₃ | CH₃ | NH | N—NO₂ | |
| 2-24 | H | CH₃ | N—CH₃ | N—NO₂ | |
| 2-25 | CH₃ | CH₃ | N—CH₃ | N—NO₂ | |
| 2-26 | —CH₂—CH₂—CH₂— | | S | N—NO₂ | |
| 2-27 | —CH₂—CH₂— | | S | N—NO₂ | |
| 2-28 | —CH₂—O—CH₂— | | NH | N—CN | |
| 2-29 | —CH₂—O—CH₂— | | N—CH₃ | N—CN | |
| 2-30 | —CH₂—O—CH₂— | | N—CH₂—CH₃ | N—CN | |
| 2-31 | —CH₂—O—CH₂— | | N—CH₂—CH₂—CH₃ | N—CN | |
| 2-32 | —CH₂—O—CH₂— | | N-n-C₄H₉ | N—CN | |
| 2-33 | —CH₂—O—CH₂— | | N—CH₂—CH=CH₂ | N—CN | |
| 2-34 | —CH₂—O—CH₂— | | N—CH₂—C≡CH | N—CN | |
| 2-35 | —CH₂—N(CH₃)—CH₂— | | NH | N—CN | |
| 2-36 | —CH₂—N(CH₃)—CH₂— | | N—CH₃ | N—CN | |
| 2-37 | —CH₂—N(CH₂—CH₃)—CH₂— | | NH | N—CN | |
| 2-38 | —CH₂—N(CH₂—CH₃)—CH₂— | | N—CH₃ | N—CN | |
| 2-39 | —CH₂—N(n-C₃H₇)—CH₂— | | NH | N—CN | |
| 2-40 | —CH₂—N(n-C₃H₇)—CH₂— | | N—CH₃ | N—CN | |
| 2-41 | —CH₂—N(CH₂—CH(CH₃)₂)—CH₂— | | NH | N—CN | |
| 2-42 | —CH₂—N(CH₂—CH(CH₃)₂)—CH₂— | | N—CH₃ | N—CN | |
| 2-43 | —CH₂—CH₂—CH₂— | | NH | N—CN | 176° C. |
| 2-44 | —CH₂—CH₂—CH₂— | | N—CH₃ | N—CN | solid |
| 2-45 | —CH₂—CH₂— | | NH | N—CN | |
| 2-46 | —CH₂—CH₂— | | N—CH₃ | N—CN | |
| 2-47 | H | CH₃ | N—CN | N—CN | |
| 2-48 | CH₃ | H | NH | N—CN | |
| 2-49 | H | H | NH | N—CN | |
| 2-50 | CH₃ | CH₃ | NH | N—CN | |
| 2-51 | H | CH₃ | N—CH₃ | N—CN | |
| 2-52 | CH₃ | CH₃ | N—CH₃ | N—CN | |
| 2-53 | —CH₂—CH₂—CH₂— | | S | N—CN | |
| 2-54 | —CH₂—CH₂— | | S | N—CN | |

What is claimed is:

1. A process for the preparation of a compound of formula

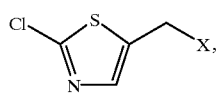

(I)

including, where applicable, an E/Z isomer, a mixture of E/Z isomers, an acid addition product and/or a tautomer thereof, in each case in free form or in salt form, wherein X is a leaving group of the formula —OS(=O)₂A; which process comprises, a) for the preparation of a compound of formula (I) wherein X is —OS(=O)₂A and A is C₁–C₈alkyl, halo-C₁–C₈alkyl, hydroxy-C₁–C₈alkyl, C₁–C₈alkoxy-C₁–C₈alkyl, unsubstituted or halo-substituted C₂–C₈alkenyl, C₂–C₄alkynyl, C₃–C₇cycloalkyl or di(C₁–C₄alkyl)amine, aryl that is unsubstituted or substituted by halogen, C₁–C₄alkyl, C₁–C₄alkoxy or by dimethylamine, or unsubstituted or halo-substituted benzyl, reacting a compound of formula

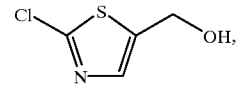

(II)

including, where applicable, an acid addition product and/or a tautomer thereof, in each case in free form or in salt form, with a sulfonylating agent;

and, in each case, if desired, converting a compound of formula (I) obtainable in accordance with the process or by another method, or an E/Z isomer, acid addition product or tautomer thereof, in each case in free form or in salt form, into a different compound of formula (I) or an E/Z isomer, acid addition product or tautomer thereof, in each case in free form or in salt form, separating a mixture of E/Z isomers obtainable in accordance with the process and isolating the desired isomer, and/or converting a free compound of formula (I) obtainable in accordance with the process or by another method, or an E/Z isomer or tautomer thereof, into a salt or converting a salt, obtainable in accordance with the process or by another method, of a compound of formula (I) or of an E/Z isomer or tautomer thereof into the free compound of formula (I) or an E/Z isomer or tautomer thereof or into a different salt.

2. A process according to claim 1, wherein

X in the compound of formula (I) is —OS(=O)$_2$A and

A is $C_1$–$C_8$alkyl, halo-$C_1$–$C_8$alkyl, hydroxy-$C_1$–$C_8$alkyl, $C_1$–$C_4$alkoxy-$C_1$–$C_8$alkyl, unsubstituted or halo-substituted $C_2$–$C_4$alkenyl, $C_2$–$C_4$alkynyl, $C_3$–$C_6$cycloalkyl or di($C_1$–$C_4$alkyl)amine, aryl that is unsubstituted or substituted by halogen, $C_1$–$C_4$alkyl or by dimethylamine, or unsubstituted or chloro-substituted benzyl.

3. A compound of formula

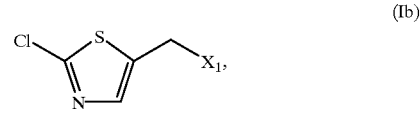

(Ib)

including, where applicable, an E/Z isomer, a mixture of E/Z isomers, an acid addition product and/or a tautomer thereof, in each case in free form or in salt form, wherein $X_1$ is —OS(=O)$_2$A and A is unsubstituted or substituted $C_1$–$C_8$alkyl, $C_2$–$C_8$alkenyl or $C_2$–$C_8$alkynyl, unsubstituted or substituted aryl, unsubstituted or substituted benzyl or di($C_1$–$C_8$alkyl)amine wherein the alkyl groups are independent of one another.

4. A compound of formula (Ib) according to claim 3, wherein $X_1$ is —OS(=O)$_2$A and A is $C_1$–$C_8$alkyl, halo-$C_1$–$C_8$alkyl, hydroxy-$C_1$–$C_8$alkyl, $C_1$–$C_8$alkoxy-$C_1$–$C_8$alkyl, unsubstituted or halo-substituted $C_2$–$C_8$alkenyl, $C_2$–$C_4$alkynyl, $C_3$–$C_7$cycloalkyl or di($C_1$–$C_4$alkyl)amine, aryl that is unsubstituted or substituted by halogen, $C_1$–$C_4$alkyl, $C_1$–$C_4$alkoxy or by dimethylamine, or unsubstituted or halo-substituted benzyl.

* * * * *